United States Patent [19]
Heanley et al.

[11] 3,995,022
[45] Nov. 30, 1976

[54] SERIAL PREPARATION OF NARROW TRACES OF CELLULAR BIOLOGICAL FLUIDS

[75] Inventors: Charles Peter Heanley, Faringdon; Jozef Kazimierz Tylko, Stoneleigh, both of England

[73] Assignee: Tetronics Research and Development Co. Ltd., Faringdon, England

[22] Filed: May 17, 1974

[21] Appl. No.: 471,072

[30] Foreign Application Priority Data
May 22, 1973 United Kingdom............... 24304/73
June 19, 1973 United Kingdom............... 28923/73

[52] U.S. Cl.............................................. 424/3; 8/3; 118/100; 118/506; 156/57; 424/7; 427/2; 427/4; 427/358
[51] Int. Cl.²..................... A01N 1/00; B05C 11/02; G01N 1/00; G01N 1/30
[58] Field of Search ................ 424/3; 118/506, 100; 156/57; 427/2, 4, 358; 8/3

[56] References Cited
UNITED STATES PATENTS
3,470,847  10/1969  Chapin............................... 118/506
3,493,447  2/1970  Rock................................... 424/3 X FOREIGN PATENTS OR APPLICATIONS
1,211,194  11/1970  United Kingdom..................... 424/3

OTHER PUBLICATIONS
Miller, A Text of Clin. Path. Williams & Wilkins, Baltimore, 7th Ed. 1966 pp. 22–29.
Todd, Clin. Diag. by Lab Methods, W. B. Saunders, Phila. 9th Ed. 1941, pp. 248–255.

Primary Examiner—Albert T. Meyers
Assistant Examiner—A. P. Fagelson
Attorney, Agent, or Firm—Dennison, Dennison, Meserole & Pollack

[57] ABSTRACT

Apparatus and method are described for preparing a narrow trace of physiological fluid on a substrate from a discrete fluid pool. The trace so produced is substantially identical to traces manually prepared in that they are characterized by distinct macroscopic and microscopic zones. Automatic trace staining apparatus also is provided.

5 Claims, 11 Drawing Figures

SERIAL PREPARATION OF NARROW TRACES OF CELLULAR BIOLOGICAL FLUIDS

The invention relates generally to apparatus and method for laying traces of biological and physiological fluids and the staining thereof. More particularly the invention relates to a method and apparatus for the laying and staining of traces of blood and its precursors and most particularly to the deposition of peripheral blood preparations as commonly used in microscopic examinations.

As will be appreciated by those skilled in the art, the automation of microscopic examinations of physiological fluids, especially as related to certain aspects of hematology automation, require highly specific and critical preparation of fluid samples prior to their microscopic examination. It has been found that techniques and apparatus as developed for the examination of exfoliated cells, as described for example in British Pat. No. 1,211,194, are not wholly suitable for either manual or mechanized examination, particularly of blood preparations. The unique nature of blood preparations and their specific diagnostic requirements necessitate the use of novel apparatus and methods which are the subject of this invention.

The orthodox and commonly used method in the preparation of blood for microscopical examinations relies on the spreading of a drop of blood with or without addition of a suitable solid anticoagulant additive such as for instance alkali salts of ethylene diamine tetraacetate on a glass slide. The success of such preparations depends chiefly on two factors, the skill of the operator and the blood properties. Blood smears prepared in this way are by no means uniform; three more or less well defined or gradually merging zones are as a rule discernible. A starting zone in which the blood film is relatively thick, a central zone in which the blood cells are fairly well dispersed but retain their shapes and, the end zone in which some of the cells are smeared-out. Each of the above three zones may be examined selectively for a variety of reasons. For example, malaria parasites are looked for in the first zone, while the second zone is commonly used for the count and differentiation of various white blood corpuscles.

Certain schools of hematology attach special importance to the third zone, in which the smeared out cells are to be found. Since the above, orthodox method is by far the most commonly practiced, it is clear that any mechanization in the preparation of blood for subsequent human examination must be able to provide all the above zones in order to be generally accepted by practicing hematologists. Notwithstanding these requirements the blood cells themselves must present in every respect the same morphological details as are seen on correctly prepared glass slides.

Blood preparations on slides prepared in orthodox ways suffer from numerous further limitations the most serious of which will be given in order to underline the advantages of our invention. By far the most serious errors occur with the most commonly used procedures, namely the differential white count, due to statistical errors. The latter is particularly important when a relatively small number of cells is counted. Since under routine conditions only one count is made, this type of error can be very serious. In addition to these fundamental difficulties, the scanning of the whole area of the deposited material on the slide in parallel rows is time consuming and small portions of the area may even be accidentally missed during such operations. There are also further difficulties arising from the weight and handling problems of glass slides.

As will be known to those skilled in the art, various methods and apparatus of depositing specimens in the form of elongated traces on glass slides and flexible films have also been described during the last 13 years. These range from manual drawing with a fine pen of blood traces to mechanized techniques which employ various means for depositing biological samples such as impactors, specially grooved spatulae, capillary tubes, felt pens, and two-bladed feeders. The mechanized apparatus of the above type frequently utilizes a reel of flexible film such as a plastic or glass tape and the associated transport for such film from one spool onto another. None of the above methods and their associated apparatus are capable of producing blood traces of the type, quality consistency and utility offered by the present invention.

This invention relates further to the staining of blood specimens as used for microscopic identification and counting of its corpuscular and other components. In current practice, blood smears or blood traces are most commonly stained according to Romanovsky's type of stains, employing numerous modifications, particularly those originally developed by Leishman. These type of stains when properly prepared and used as recommended by the stain makers are capable of differentiating inter alia: leucocytes, and impart characteristic colors to leucocyte's nuclei; neutrophilic, eosiniphilic and basophilic granules; lymphocyte cytoplasm and nuclei; lymphoblasts, platelets, erthrocytes, myelocytes, monocytes, and their precursors; also Auer bodies, variety of inclusion bodies, bacteria, rickettsiae, and malarial and other parasites.

In order to appreciate some of the advantages of the present invention it shall be sufficient to mention that when Romanovsky type of stain are finally compounded and ready for use, they are themselves in a state of complex reactions taking place between the stain constituents, the kinetics of which are greatly affected by such factors as the state of dilution, exposure to air, concentration of the dissolving media and others. Hence it will be appreciated that in order to achieve consistent results not only the staining procedure should be precisely defined, but preferably also the washing procedure that follows the staining. The present invention provides a method and apparatus by means of which extremely consistent, rapid staining can be achieved, giving all the necessary differentiating characteristics derived from the orthodox procedure. The invention will be described particularly with reference to the following drawings in which:

Figure 1:
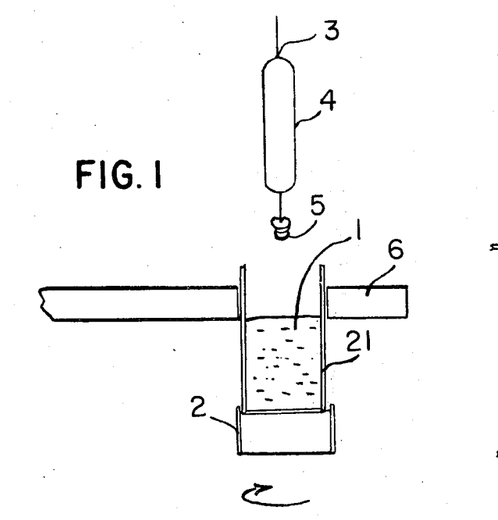
FIG. 1 is an illustration of the fluid depositing apparatus.
Figure 2:
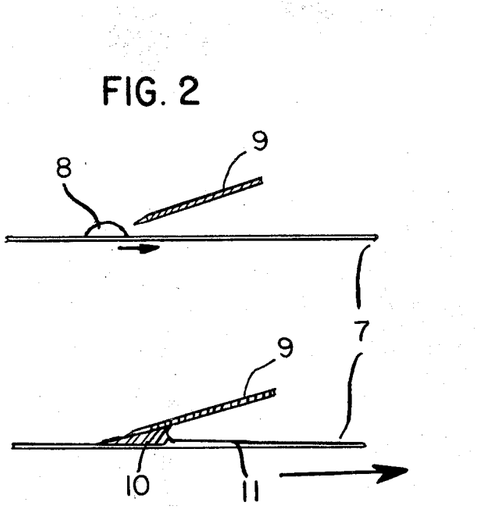
FIG. 2 is a view of the relationship of the fluid pool and fluid extending means before and after contact.

According to one aspect of the invention, a method of preparing blood or its precursors for microscopic examination comprises the steps of depositing a discrete quantity of blood 8 upon a transparent film 7, coacting the said blood with a blade 9 as hereinafter defined and spreading the blood in a substantially elongated path from a liquid index 10 established between the juxtaposed surfaces of the film and the blade. Conveniently, the discrete quantity of blood is taken from a container 21 by immersing in it a pin 3 directed with its head downward. Upon withdrawing the pin 3, a small quantity of blood will be retained in a form of a sessile drop 5. The pin 3 with the sessile drop 5 is then lowered onto the surface of a transparent film 7 depositing upon it a discrete pool of blood 8. After the pin 3 is removed, the pool of blood 8 is made to contact the tip of a blade 9. The blade 9 is maintained in an oblique position so that an acute angle is formed between the lower surface of the blade 9 and the plane containing the surface of the film 7, as shown in FIG. 2. Once the contact between the blood pool 8 and the tip of the blade 9 is established, a liquid index of blood is formed and maintained between the lower surface of the blade and the film surface. By virtue of establishing this index which can be formed by touching only the pool 8 without touching the film surface, a stable reservoir of blood 10 is created which is connected with the originally deposited pool. When a subsequent movement between the film 7 and blade 9 takes place a characteristic elongated trace 11 of gradually thinning-out width is obtained.

The blade 9 may be constructed of any suitable material but it is preferred that it is made from a semirigid but flexible plastic material. It should be of suitable dimensions to form a narrow trace when contacted with the pool of blood 8 and subsequently moved. A narrow tapering piece of plastic material with a fine tip is therefore preferred and this may be mounted in a rigid support.

The method as described above leaves a trace of characteristic macroscopic appearance while its microscopic appearance is substantially the same as that of glass slides correctly prepared by smearing. Thus all the expected forms are encountered in the respective zones as mentioned in the introductory remarks and furthermore all the blood forms are well separated. It is important to stress that the success of the above method is related to its directional properties, namely the trace issues from the thick portion of the index. Experimental evidence consistently shows that traces prepared in the above manner fulfill all the rigorous requirements of hematological examinations and in addition offer much smaller statistical errors in counting cells than those encountered on glass slides.

It also falls within the compass of the invention to provide means of stirring blood prior to the collection of the specimen. Such means may conveniently include rotation of the sample containers while mounting or incorporating on the shaft of the pin a suitable blade or blades.

Since one of the important objects of the invention is to provide mechanization, means for enabling the trace laying procedures to be repeated are also provided.

Another aspect of the invention comprises a method of washing and drying of the pin and blade. Thus when the pool of blood has been deposited the pin with the stirrer mounted upon it are subjected to the action of a jet of water followed by a jet of drying air. Similarly, after the blade completes its trace laying operation it is subjected to the action of a jet of water followed by a jet of air. According to another aspect of the invention pre-marked reels of film are used for laying serially the traces of blood, the marking defining the length of the traces and the intervals between them while the traces and the operations associated with their serial production are made responsive to the markings carried by the film. In addition to the above markings the film may conveniently carry serial numbers and/or letters identifying each trace, such alphanumerics being used in order to eliminate any mistakes arising in the trace-patient correspondence. The fixing and the drying of the blood traces falls also within the scope of the invention and is carried out by passing the film through a suitable fixative medium such as methyl alcohol and exposing it afterwards to a stream of air. Alternative fixatives such as a stream of hot air may also be practiced. The fixed and dried blood traces laid on the film may be now stained by any of the Romanovsky type stains or other stains but a preferred method and apparatus for staining the above type of blood traces is described hereinbelow.

Figure 3:
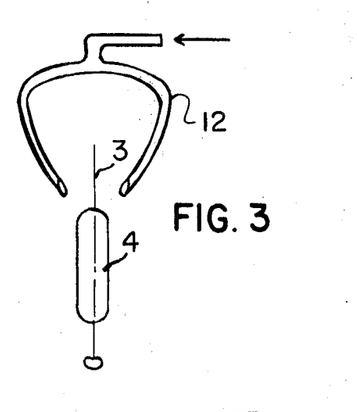
FIG. 3 is an illustration of the washing apparatus.
Figure 4:
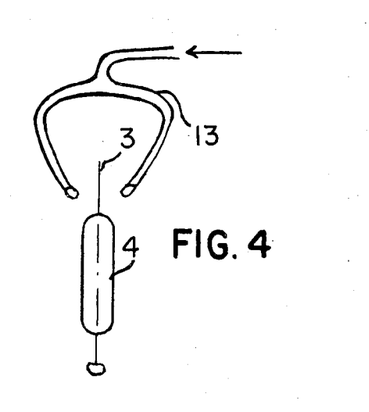
FIG. 4 is an illustration of the drying apparatus.

FIGS. 3 and 4 show diagrammatically the pin 3 with the stirrer 4 brought to the washing station 12, and drying station 13. The blade is similarly washed and dried but this is not shown.

Figure 5:
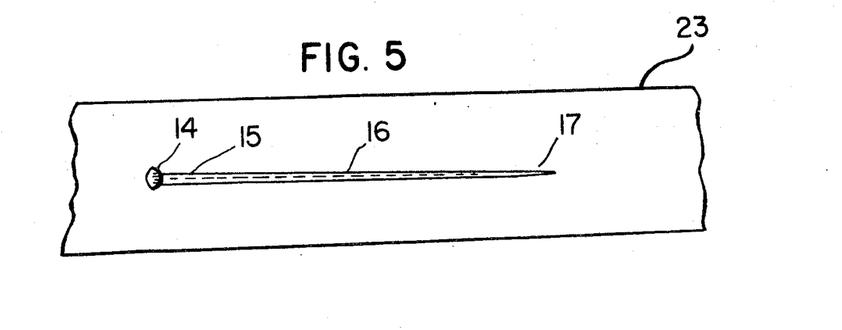
FIG. 5 is an illustration of a completed fluid trace.

FIG. 5 shows diagrammatically a trace of blood as prepared according to the invention. In the sword like shape of the trace one may discern the arc portion 14, being the residuum of the blood pool 8, the slightly thicker portion 15, corresponding to the first zone, the middle portion 16, corresponding to the second zone and the somewhat thinned end portion 17, corresponding to the third zone.

Figure 6:
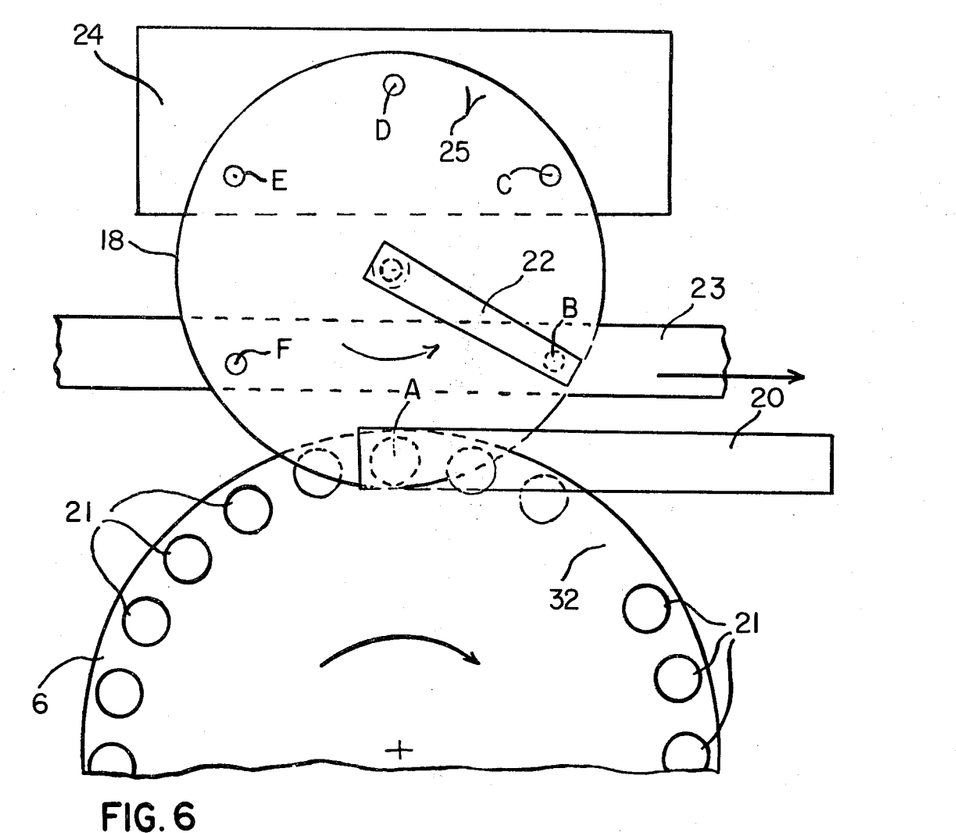
FIG. 6 is one preferred arrangement of the fluid depositing and fluid extending apparatus.

The detail of apparatus arrangement shown in FIG. 6 represents one variant of the invention in which, the two peripherally overlapping discs 6 and 18, are the turntable carrying the blood containers and the pins (with stirrers) and trace laying blades turntable, respectively. The turntable 6 carries peripherally equispaced openings for the blood containers but for one blank space 32, the latter corresponding to the completion of the laying of the respective traces from all the blood containers placed in each opening of the turntable. The turntable 18, on the other hand, has six peripherally equispaced stations carrying alternately three pins and three blades. Both turntables are interlinked and capable of stepwise rotation in response to a conventional geneva mechanism driven by a motor. The turntable 6 advances one step, i.e. from one blood container to the next corresponding to laying of one trace, while the turntable 18 advances through two steps namely those involving the actuation of the pin 3, and the blade 9. The vertical component of the movement of the pin 3 is provided by member 20; the same mechanism energized by the same motor may also be utilized to raise vertically the platform upon which the blood container 21 rests. This arrangement is particularly useful since it permits the use of blood containers of different lengths. Conveniently, when the circumferential motion of the pin ceases, and the pin 3 finds itself directly above the blood container 21, the pin 3 with its stirrer 4 descends while the blood container 21 is rotated by independent means (not shown).

In order to understand the sequence of operations taking place on the turntable 18, the stations A–F corresponding to the three peripherally equispaced pins with stirrers and three peripherally equispaced trace laying blades will now be described. The turntable 18 rotates stepwise in an anticlockwise mode as shown. At station A the blood container 21 is rotated and if required may also be raised; the pin 3 and its stirrer 4 are lowered and thereby the blood is stirred. Also at this station the pin 3 is withdrawn and the blood container 21 brought to rest (and lowered to its original position in case it was necessary to raise it).

Upon the next stepwise movement the pin 3 arrives at station B where the bar 22 depresses the pin 3 downward so as to deposit the sessile droplet of blood 5 upon the surface of a transparent film 23, resulting in the deposition of a blood pool 8 upon the film's surface. During this operation the film 23 is stationery. Also at station B the pin is raised upward. All the movements of the pin 3, carried out at station B are energised through a concentric shaft actuated also by the geneva mechanism (not shown) referred to before. When the turntable 18 rotates through the next step to station C the pin 3 with its stirrer 4 enters into the washing and drying chamber 24, shown diagrammatically as a rectangular compartment embracing stations C, D, and E. Station C comprises a washing chamber substantially as shown in FIG. 3 where a plurality of water jets derived from a reservoir (not shown) are made to impinge upon the pin 3 and its stirrer blade 4. While moving to station D, the pin 3 and the stirrer blade 4 impinge elastically on a spring loaded protruding member 25 which shakes off any residual droplets of the water that may be adhering to the pin 3 or its blade 4. According to one aspect of the invention as shown in FIG. 6, stations D and E provide two separate drying chambers substantially as shown in FIG. 4 while station F is a station at which the pin 3 or trace laying blade 9, whichever the case may be, are resting in readiness. One step behind the pin 3 and its stirrer 4 moves the blade 9, mounted at a preset angle so as to make contact with the blood pool 8 when reaching the station B. When the blade 8 reaches station B, the film 23 advances in the direction of the arrow X through a preset distance and at a substantially uniform speed controlled by a transport mechanism (not shown). Having completed its blood trace laying (see FIG. 5) the blade 9 moves to the washing chamber at station C while the film 23 moves through a preset distance so as to provide a fixed spacing between the blood traces.

The sequence of operations as hereinabove described proceeds advancing a new blood container 21, from the turntable 6, until the last blanked position 32 is reached, whereupon a signal is provided indicating that new blood containers may be inserted.

Figure 7:
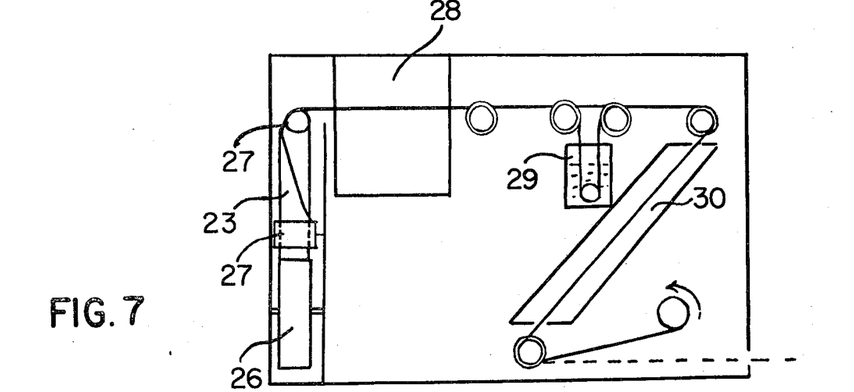
FIG. 7 is a view of an apparatus used with the apparatus of FIG. 6 for continuous and automatic preparation of fluid traces.

FIG. 7 shows one possible arrangement of the components of the present invention. The spool with the pre-marked transparent film 26 is unwound through a half-twist over the pulleys 27, the trace laying assembly 28 (as shown in FIG. 6), into the fixing chamber 29 containing methanol, and therefrom into the drying chamber 30 in which preheated air is made to circulate. Upon leaving the drying chamber 30 the film 23 may either be spooled on the spool 31, as provided, or, alternatively, the film 23 with its traces may be passed directly into the trace staining apparatus.

According to another aspect of the invention an apparatus for staining blood specimens is provided comprising: means for transporting at uniform velocity a train of blood specimens along an inclined path; means for metering and mixing constituents of a stain and a buffered diluent; means for contacting the said compounded and diluted stain with the said moving train (in a cocurrent mode) over a fixed distance; means for jetting water upon the said train of specimens so as to form a pool and means for withdrawing the collecting liquids at a downstream point at a height and rate maintaining a constant level of liquid in the said pool; means for withdrawing the said train of specimens from the said pool; and means for drying the said train of specimens. The method of staining blood specimens according to Romanovsky's type of stains comprises continuously mixing small metered quantities of the concentrated constituents of the said stains with simultaneously metered buffered diluent; allowing the resulting mixture to impinge as a stream upon the (moving) surface of said specimen; maintaining the said stain in contact with the said specimen over a fixed distance; forming and maintaining a constant level water pool and making the said specimen pass through the said pool and drying the said specimen in a stream of warm air.

The train of specimens subjected to the staining procedure above may be presented in several different manners. For example, they may be formed by a linked train of glass slides, on which the specimens have been deposited, carried in a flexible holder. The specimens are then moved by movement of the holder through the various stages of staining and washing. Alternatively, the specimens may be linearly spaced on a narrow strip of flexible plastic film material and the material moved through the stages of staining and washing. Other means of transporting a train of specimens through these procedures will be apparent to those skilled in the art and it is not intended that the present invention should be limited to one particular method.

The present method is particularly advantageous where it is first necessary to mix constituents of a stain before it is applied to the specimens. Conventionally, the constituents are mixed in bulk and the mixture is used on a given number of specimens until it is considered exhausted or unsatisfactory. As the stain may deteriorate during this period of use, those samples stained earliest after the stain is mixed will appear different from those stained just before the stain is discarded. Consequently the appearance of stained specimens may differ and make comparison between them difficult. In contrast the constituents of the stain, according to the present method, are mixed and immediately applied to the specimen. The stain applied to the specimen has always been mixed for only a short and for the same time for each specimen. It is found that the freshly mixed stain is more active in staining than stain which has been mixed for some time, thereby allowing short staining times. Further all specimens receive stain which has been mixed for the same time and therefore are consistently stained.

The particular stain which is mixed and applied to the specimens is not critical to the present invention and will depend on the preference of the particular user. It is found that certain stains are preferred by different users and by users in particular countries. The preparation of solution of constituents of these stains will be known to those skilled in the art, as will the proportions in which they are mixed. These solutions and proportions may be altered to impart particular staining characteristics to the mixture and such preferred combinations may be determined by experimentation.

It has further been found that the manner in which the stained specimens are washed is critical to achieve satisfactory and consistent staining. Consequently the present method also provides a method of washing the stained specimens comprising applying water to the specimens in a manner that retains a pool of water through which the specimens move and simultaneously removing water from that pool. In the case of specimens carried on glass slides, this may be achieved by running water on to the specimens as they pass into a reservoir, allowing the water to collect in the reservoir, and withdrawing water from the reservoir at the same rate at which it is added. This procedure applies fresh water to each specimen and maintains each specimen in contact with a pool of water for a given period of time.

The present apparatus comprises means for mixing metered quantities of constituents of the stain, with suitable buffer solution, and means for delivering the mixed stain to the specimen. For example, metered quantities of stain constituents and buffer solution may be pumped into a reservoir and mixed. The mixed stain is allowed to drain from the reservoir directly on to the specimens, delivered as described before. By careful metering of the flow of each constituent and the buffer, it is possible to control both the proportions of the constituents in the final stain, and the rate at which the stain is applied to the specimens.

It is preferred that the stain is applied directly to the surface of the specimens while these are moving. This may be achieved by applying a stream of mixed stain to the train of specimens while this is moving in a downward direction at approximately 45° to horizontal. By this means, the stain applied to each specimen remains substantially in contact with that specimen until it is washed from the surface.

The present method is ideally suited to automation of staining procedures and means may be provided for automatically passing the specimens through the stages of washing and staining, thereafter drying the specimens in a current of warm air and collecting the specimens. For example, when specimens are carried on glass slides which are moved by means of a flexible carrier, the slides may finally be collected in order and selected into batches, in preparation for examination. Alternatively, where specimens are carried on strips of flexible material, these may be rolled onto a spool for subsequent examination. This latter method is of particular advantage where the specimens are laid on the strips by automatic means.

The invention will now be described with reference to FIG. 8, using by way of example a procedure involving one of the more commonly used Romanovsky's stain variants, namely the May-Grünwald-Giemsa Stain.

Figure 8:
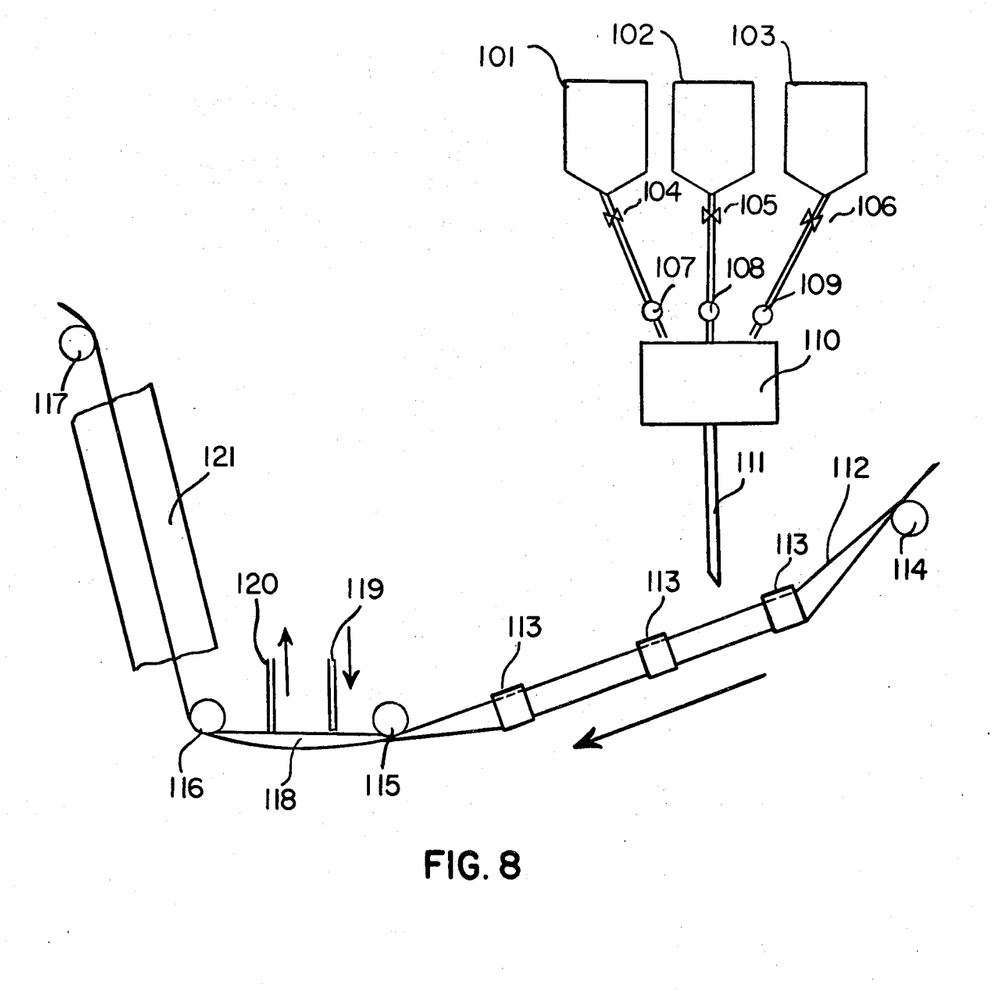
FIG. 8 is a schematic view of the staining assembly.

FIG. 8 shows diagrammatically an apparatus for staining blood traces in which three vessels, 101, 102 and 103, are used for storing concentrated May-Grünwald-Giemsa stain and water buffered to pH 6.8, respectively. Each of these containers carries in its exit lines non-return valves 104, 105 and 106, respectively, followed by three peristaltic pumps 107, 108 and 109, respectively. All the three lines lead to a mixing chamber 110, provided with an exit line in a form of a hypodermic needle 111. Transported immediately below the needle 111 is the film 112, carrying the blood traces. This film is pressed inwardly at the edges by a number of formers 113 which impart to it a trough shape. Conveniently the formers 113 comprise guide blocks having a V-shaped groove therein, through which the film passes to form a V-shaped trough. The film is transported over the rollers 114, 115, 116 and 117, in the direction indicated. Rollers 115 and 116 define the constant level washpool 118 which is filled by a tube 119 and evacuated by a suction line 120. Having passed the washpool 118, the film with the blood traces upon it enters into a drying chamber 121 through which a stream of warm and dry air is passed.

It will be apparent to those skilled in the art that the above apparatus may be adapted to the staining of blood smears on conventional glass slides by placing the latter on a suitably ribbed belt and augmenting the flows.

According to yet another aspect of the present invention the staining of blood traces or blood smears to the May-Grünwald-Giemsa Stain, comprises preparing the constituents of the said stain in three separate vessels using proprietary powdered stains as sold by Messrs. Gurr Ltd. Thus, there is prepared May-Grünwald, 8 grams of powdered stain in 2½ liters of methanol; Giemsa, 16 grams of powdered stain in 1 liter of methanol and in 1 liter of glycerol; and buffered water to pH 6.8, using Sorensons phosphate as buffer. The above 3 constituents are mixed in a ratio: 3 parts V/V buffered water to 1 part V/V Giemsa stain, to 1 part V/V May-Grünwald. The resulting stain is fed upon the blood traces at a rate of 1 ml./min., while the traces move at a rate of 30–35 cm./min. The distance over which the stain and wash is applied being 61 cm. Hence, the above method achieves staining in 102 seconds, instead of the usual 20 minutes which this type of stain requires.

While the exact reasons for successful speeding of the staining action in the present invention is not fully understood, the following factors are considered to be chiefly responsible:

a. large area of stain is exposed to air (and oxygen);
b. the methanol azeotrope evaporates rapidly concentrating the stain;
c. fresh stain is continuously delivered to the specimens;
d. enhanced evaporation from the surface brings more of the stain into contact with specimen;
e. under the prevailing dynamic conditions, the glycerol content of the Giemsa stain releases its dissolved stain to the methanol and water present;
f. the very short time of interaction between mixing the components and washing off the stain prevents the stain from harmful precipitation.

Yet another advantage of the present invention lies in using standard individual stains while mixing them and diluting only just prior to use, thus guaranteeing long life without deterioration, and a consistency of staining particularly required in automated analysis.

An especially preferred embodiment of this invention is described hereinbelow, particularly with reference to FIGS. 9–11, and is a combination of the trace laying apparatus and the staining apparatus.

Figure 9:
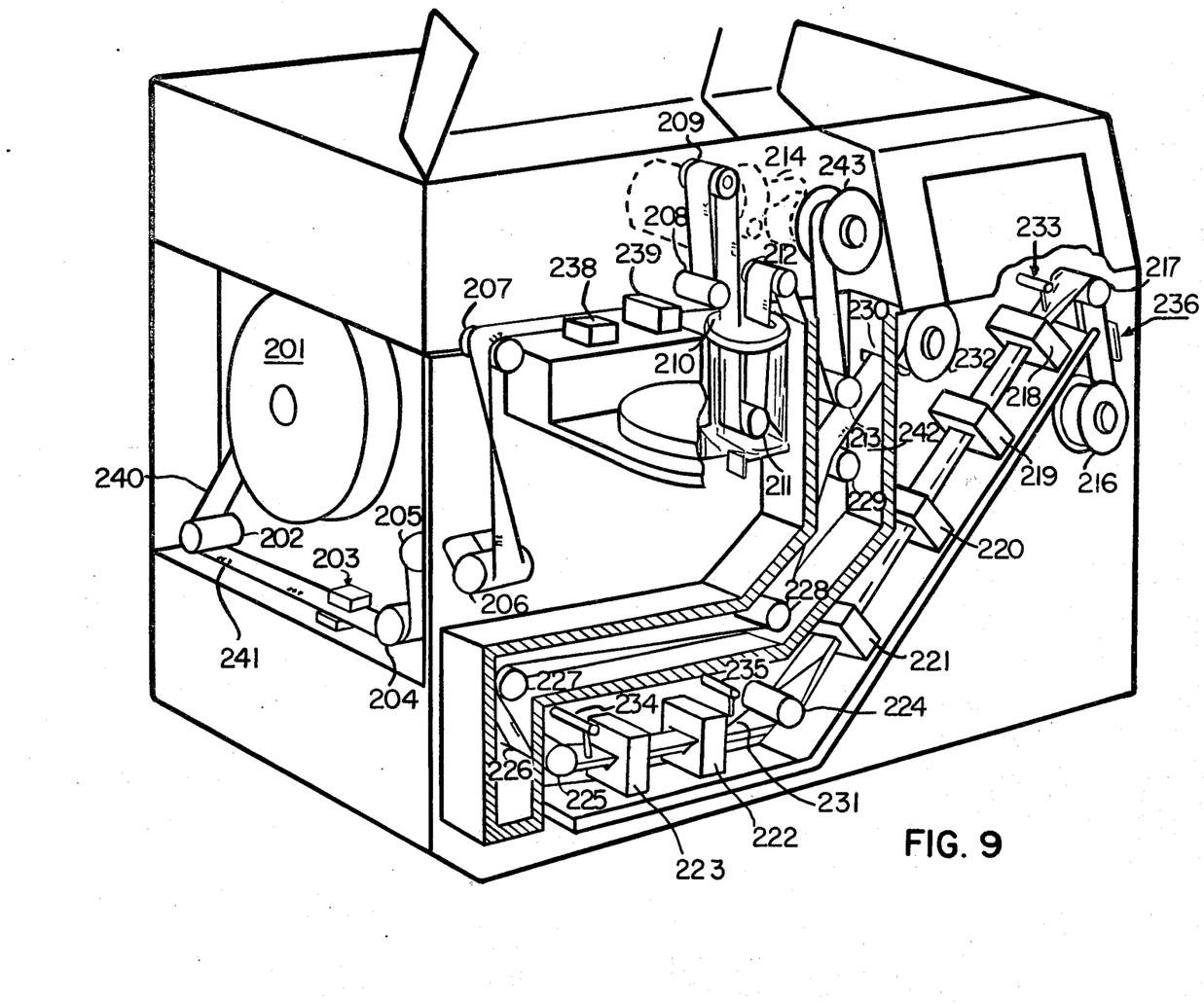
FIG. 9 is a schematic, partially in section, of the combined laying and staining assembly with a portion of the laying mechanism removed for clarity.

With reference to FIG. 9, film feed spool 201 has trace receiving means 240 wound thereon. The trace receiving means 240, preferably a continuous transparent film having identifying indicia 238 at spaced intervals capable of being read by reading 203, functioning as a trace recall detector, is threaded from feed spool 201 over guide reel 202 through the reading head 203, then over guide reels 204, 205, 206 and 207 past a numerical display window 238. For clarity, the trace laying mechanism described in FIGS. 10 and 11 has been removed from the apparatus described in FIG. 9.

Figure 10:
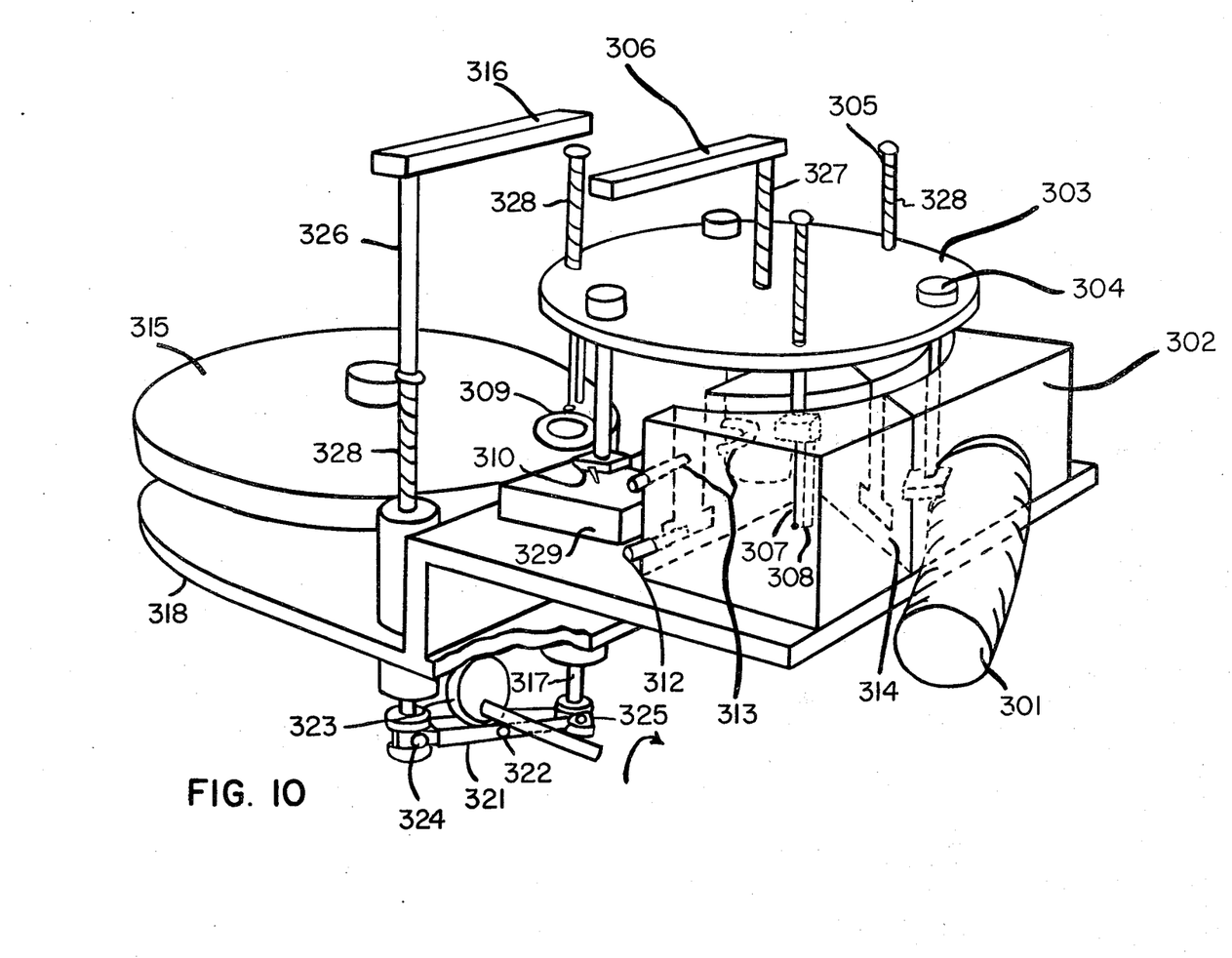
FIG. 10 is a view of the automatic trace laying apparatus.
Figure 11:
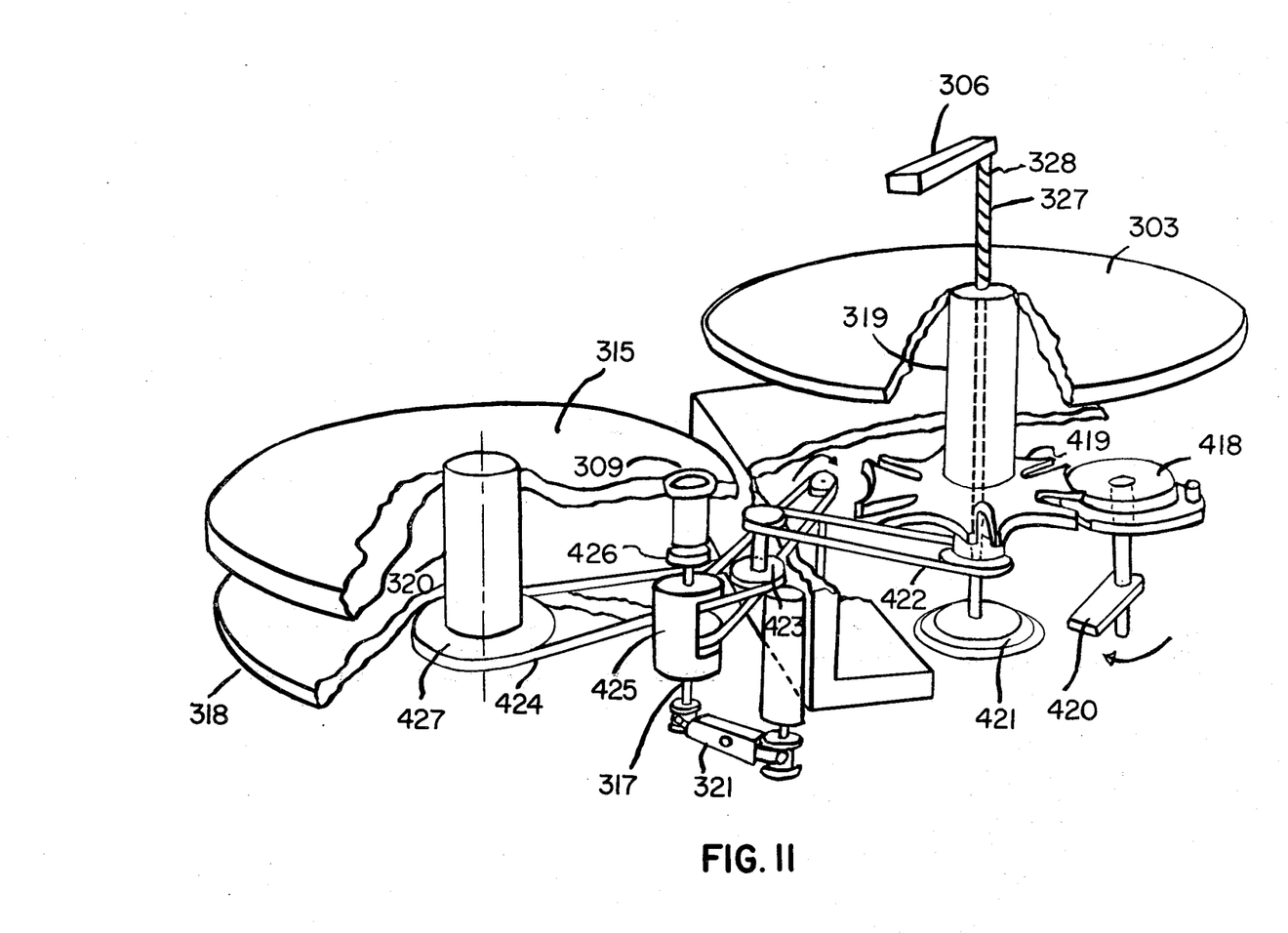
FIG. 11 is a view of the driving and indexing means for the trace laying apparatus utilized in one embodiment of the present invention.

From numerical display window 238 the trace receiving film passes over and is supported by laying point block 239 where, when the trace laying apparatus illustrated in FIGS. 10 and 11 is in position, a trace of the fluid sample is applied to film 240. The film having a trace thereon then proceeds via guide reels 208, 209, 211 and 212 through a fixing chamber 210 containing a fixing fluid, commonly methanol. Film 240 then passes into a drying chamber 242 over guide reel 213 to film take-up spool 243, driven by laying film drive motor 214.

Further with reference to FIG. 9, film 240, having a fluid trace thereon and being wound on a staining feed spool 216 and guided by film guide 236 is threaded through V-guide blocks 218, 219, 220 and 221, which upraise the lateral edges of film 240 and cause the formation of a V-shaped trough therebetween. The V-guide blocks are arranged in an inclined manner and stain from stain delivery point 233 is applied to the film as it passes delivery point 233. The stain is retained in the formed trough as film 240 moves downwardly through the V-guide blocks and over reel 224. Water is added to the trough at water delivery point 235 and removed at effluent extractor 234. In that interval the trough form is retained by means of V-guide blocks 222 and 223. Film 240 then proceeds over guide reel 225 through slit 226 into the drying chamber 242. Guide reels 221, 228 and 229 direct the film through the drying chamber and out by means of slit 230 to take-up spool 232.

At the position of laying point block 239 is attached the automatic trace laying apparatus illustrated, in one embodiment, in FIGS. 10 and 11. As shown therein, base member 318 supports two rotatable members 315 and 303. Conveniently, members 303 and 315 are disc shaped and are supported on base 318 by column members 319 and 320, respectively, which rotate relative to the base 318, thereby rotating members 303 and 315. Members 303 and 315 are moved relative to one another by means of a conventional Geneva drive mechanism which also functions as an indexing means. Driving wheel 418, powered by a motor (not shown), drives wheel 419, which is connected via transmission belts 422 and 424, through idler mechanism 423, to carousel driving wheel 427, which serves to drive member 315.

Mounted on member 315 are a plurality of sample containers 309 (only one of which is shown) which contain the fluid from which a trace is to be prepared. Mounted on member 303 are a plurality of pin holders 305 and a plurality of blade holders 304, alternately disposed around the periphery of disc 303. Pin holders 305 are biased in a raised position by biasing means 328, preferably compressed spring members retained between the surface of disc 303 and the top portion of pin holders 305. The top portion of pin holders 305 conveniently is flanged in order to retain the spring member 328.

Pin holders 305 are lowered into sample container 309 by downward movement of member 316 connected to shaft 326. That downward movement is effected by the action of cam means 323 acting on member 321 which is pivotable about point 322. Member 321 is pivotably connected to shaft 326 at point 324. Cam means 323 is made to rotate by independent means (not shown), thereby downwardly moving shaft 326 and causing member 316 to contact and downwardly move pin holder 305 into contact with the fluid retained in sample container 309.

At the same time pin holder 305 is lowered into sample container 309, optional means are provided to raise sample container 309 while simultaneously rotating the sample container. Raising of container 309 is accomplished by the action of cam means 323 on member 321 which can be pivotably connected to shaft 317 at point 325. As can be seen most easily in FIG. 10, cam means 323 is offset from pivot point 322 and is located between pivot points 324 and 322. Thus, when cam means 323 depresses member 321, with consequent lowering of shaft 326, member 321 effects the upward movement of shaft 317 through its connection thereto at pivot point 325. Connected to shaft 317 is member 426, shown in FIG. 11, which serves to contact sample container 309 and bring it to its upraised position. Further, as shown in FIG. 11, means are provided for rotating shaft 317, these means comprising a belt driven disc connected to shaft 317 and contained in housing 425. Stirring member 308 mounted on pin holder 305 serves to stir the fluid in sample container 309 when the sample container is rotated. Independent means (not shown) are provided for rotating the drive belt.

Upon rotation of cam means 323 out of contact with member 321, spring 328 forces shaft 326 upwardly, thereby moving member 316 out of contact with pin holder 305. The action of spring 328 on shaft 326 also lowers shaft 317 through the action of pivot arm 321 to move member 426 out of contact with sample container 309.

Spring 328 connected to pin holder 305 then forces upwardly member 305 to remove the pin from sample container 309, the pin having a discrete quantity of fluid in the form of a sessile drop clinging thereto. Further rotation of member 303 places loaded pin holder 305 in position over laying block 239 having a film passing thereover.

Pin holders 305 are lowered onto the film by means of member 306 which is supported on shaft 327 having similar spring means 328. As can be seen most clearly from FIG. 11, as driving wheel 418 rotates, member 420 mounted on a shaft connected thereto impinges on disc 421, which has an inclined upper surface. As member 420 proceeds along the inclined surface, a downward movement of shaft 327, connected to disc 421, is effected. Member 306 contacts pin holder 305 when the pin holder is under member 306, forcing it downward to deposit a discrete fluid pool on the surface of a film passing over laying block 239. When member 420 has passed over the inclined surface of disc 421, spring 328 raises shaft 327 and member 306 to a raised position out of contact with said film.

Further rotation of member 303 places blade 310 connected to blade holder 304 in contact with the fluid pool previously deposited on the film. When blade 310 is in contact with the fluid, the film is moved a predetermined distance, thereby extending the fluid on the film, in the manner described previously, to produce a fluid trace having the aforementioned desired characteristics.

When the trace has been completed, members 315 and 303 are rotated to bring another sample container in position under a correctly positioned pin holder and the process is repeated.

As can be seen from FIG. 10, pin holders 305 and blade holders 304 pass into a washing chamber during rotation of members 303. There they are washed by washing means 312 and 313 and then dried in drying chamber 302, warmed air being fed via tube 301, upon further rotation of member 303. The drying and washing chambers conveniently are separated by member 314 having appropriately shaped cut-outs at its entrance and exit for passage of members 305 and 304.

The foregoing description of the preferred embodiments of the present invention is presented for illustration and is not intended to limit the invention thereto. Various modifications will be apparent to those skilled in the art without departing from the spirit or scope of this invention.

What we claim is:

1. In a method of laying serially traces of a generally cellular biological fluid on the surface of a trace receiving means comprising a flexible continuous transparent film which comprises with regard to each trace the improvement comprising the steps of:

a. depositing a discrete quantity of said fluid in the form of a sessile drop on the surface of said receiving means, thereby forming a discrete pool of fluid;
   b. contacting said fluid pool with a fluid extending means having a fine tip to establish a liquid index of said pool of fluid between said tip of said extending means and the surface of said trace receiving means; and
   c. moving said fluid extending means and said receiving means relative to each other, whereby said fluid is retained between the surface of said receiving means and said extending means to effect a narrow trace of gradually thinning-out width of said fluid on said surface of said receiving means.

2. The method of claim 1 wherein said extending means has a blade portion inclined downwardly toward the surface of said receiving means in a direction opposed to the direction of the fluid trace.

3. The method of claim 2 wherein the fluid trace is produced by holding the blade portion stationary and moving the trace receiving means.

4. The method of claim 1 wherein the spatial relationship of said extending means and said trace receiving means is such that said means are out of contact with each other but are so proximate as to effect a fluid trace having three gradually merging zones from relatively thick to thin.

5. The method of claim 1 which further includes the steps of fixing and drying said fluid trace.

* * * * *